United States Patent
Iyer et al.

(10) Patent No.: US 7,187,535 B1
(45) Date of Patent: Mar. 6, 2007

(54) MULTIPOLAR FEEDTHROUGH ASSEMBLY WITH CUSTOMIZABLE FILTER AND METHOD OF MANUFACTURE

(75) Inventors: Rajesh V. Iyer, Eden Prairie, MN (US); Daniel J. Koch, Lakeville, MN (US); Shawn D. Knowles, Saint Francis, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/343,109

(22) Filed: Jan. 30, 2006

(51) Int. Cl.
 *H01G 4/35* (2006.01)
 *H01G 4/228* (2006.01)

(52) U.S. Cl. .................. 361/302; 361/307; 361/306.1; 607/5

(58) Field of Classification Search .................. 174/50, 174/50.5, 520, 650, 262, 152 GM; 361/307, 361/302, 306.2, 328, 329, 306.1; 607/5
See application file for complete search history.

(56) References Cited

U.S. PATENT DOCUMENTS

| | | | | |
|---|---|---|---|---|
| 3,808,478 A | * | 4/1974 | Winkler | 361/302 |
| 5,032,692 A | * | 7/1991 | DeVolder | 361/302 |
| 5,905,627 A | * | 5/1999 | Brendel et al. | 361/302 |
| 6,414,835 B1 | * | 7/2002 | Wolf et al. | 361/302 |
| 6,566,978 B2 | * | 5/2003 | Stevenson et al. | 361/302 |
| 6,643,903 B2 | * | 11/2003 | Stevenson et al. | 361/302 |
| 6,765,779 B2 | * | 7/2004 | Stevenson et al. | 361/302 |
| 6,850,405 B1 | * | 2/2005 | Mileham et al. | 361/302 |
| 7,035,077 B2 | * | 4/2006 | Brendel | 361/302 |
| 7,113,387 B2 | * | 9/2006 | Stevenson et al. | 361/302 |

* cited by examiner

*Primary Examiner*—Angel R. Estrada
(74) *Attorney, Agent, or Firm*—Carol F. Barry; Girma Wolde-Michael

(57) ABSTRACT

A feedthrough assembly for guiding a plurality of terminal pins through the housing of an implantable medical device. The feedthrough assembly comprises a ferrule fixedly coupled to the housing and having an aperture therethrough, and a non-conductive supporting structure fixedly coupled to the plurality of terminal pins and disposed within the aperture. The supporting structure is configured to guide the plurality of terminal pins through the ferrule. A plurality of capacitors, which is fewer in number than the plurality of terminal pins, is fixedly coupled to the supporting structure and electrically coupled between the ferrule and selected ones of the plurality of terminal pins.

10 Claims, 8 Drawing Sheets

MULTIPOLAR FEEDTHROUGH ASSEMBLY WITH CUSTOMIZABLE FILTER AND METHOD OF MANUFACTURE

TECHNICAL FIELD

This invention relates generally to implantable medical devices and, more particularly, to a multipolar feedthrough assembly with a customizable EMI filter for utilization with an implantable medical device.

BACKGROUND OF THE INVENTION

Cardiac pacemakers and other such implantable medical devices (e.g., cochlear implants, neurostimulators, active drug pumps, etc.) typically comprise a hermetically sealed container and a feedthrough assembly having one or more feedthrough terminals (e.g., niobium pins) that provide conductive paths from the interior of the container (e.g., from an anode lead embedded in an internal anode) to one or more lead wires exterior to the device. In the case of a cardiac pacemaker, these lead wires conduct pacing pulses to cardiac tissue and/or sense cardiac rhythms. To reduce the effects of stray electromagnetic interference (EMI) signals that may be collected by lead wires coupled to the feedthrough terminal pins, it is known to equip a feedthrough assembly with an EMI filter comprising a capacitor that permits passage of relatively low frequency electrical signals along the terminal pins while shunting undesired high frequency interference signals to the container.

Two types of capacitors are generally used: chip capacitors and discrete or monolithic discoidal capacitors. Chip capacitors typically comprise a rectangular ceramic monolithic that is fixedly coupled (e.g., glued) to the ferrule to electrically couple the ferrule to a terminal pin. Such capacitors are fairly inexpensive and occupy a relatively small volume in an implantable medical device. However, chip capacitors are effective for filtering EMI signals over a relatively narrow band of frequencies and, consequently, are fairly limited in application.

Discoidal capacitors have been developed as an alternative to chip capacitors. In the case of a feedthrough assembly comprising a single terminal pin (i.e., a unipolar feedthrough assembly), a discrete discoidal capacitor may be utilized that includes a terminal pin aperture therethrough configured to receive the terminal pin. In the case of a feedthrough assembly comprising multiple terminal pins (i.e., a multipolar feedthrough assembly), a monolithic discoidal capacitor is utilized that includes a plurality of terminal pin apertures therethrough each configured to receive a different terminal pin. In contrast to chip capacitors, discoidal capacitors are effective for filtering EMI signals over a relatively broad range of frequencies; however, monolithic discoidal capacitors are relatively large and expensive to produce.

It may be desirable to leave one or more terminal pins within a multipolar feedthrough assembly unfiltered, such as, for example, those which act as RF antennas to permit communication with the implantable medical device. Additionally, it may also be desirable to equip the various feedthrough terminal pins of a multipolar feedthrough assembly with varying degrees of EMI protection depending upon, for example, the electrical tolerance of the circuitry associated with a particular pin and/or the susceptibility of each pin to EMI interference. In an implantable pacemaker/defibrillator comprising six terminal pins, for example, four pins may be utilized for low-voltage (e.g., around 12 volts) sensing/pacing, while the remaining two pins may be utilized for high-voltage (e.g., around 850 volts) defibrillation. Thus, the four sensing/pacing pins each require only a low-voltage capacitor, while the two defibrillation pins require each a larger, high-voltage capacitor. Traditionally, such a feedthrough assembly has been outfitted with a unitary, high-voltage monolithic capacitor as described above that provides EMI filtering for each of the six terminal pins, including the four low-voltage terminal pins. This may result in an increase in volume and cost that is functionally unnecessary.

Considering the above, it should be appreciated that it would be desirable to provide a multipolar feedthrough assembly having a customizable EMI filter and a method for manufacturing such a feedthrough assembly. Furthermore, other desirable features and characteristics of the present invention will become apparent from the subsequent detailed description of the invention and the appended claims, taken in conjunction with the accompanying drawings and this background of the invention.

SUMMARY OF THE INVENTION

A feedthrough assembly for guiding a plurality of terminal pins through the housing of an implantable medical device. The feedthrough assembly comprises a ferrule fixedly coupled to the housing and having an aperture therethrough, and a non-conductive supporting structure fixedly coupled to the plurality of terminal pins and disposed within the aperture. The supporting structure is configured to guide the plurality of terminal pins through the ferrule. A plurality of capacitors, which is fewer in number than the plurality of terminal pins, is fixedly coupled to the supporting structure and electrically coupled between the ferrule and selected ones of the plurality of terminal pins.

A method is provided for customizing an electromagnetic interference filter for use in a feedthrough assembly fixedly coupled to the housing of an implantable medical device and configured to guide a plurality of terminal pins therethrough. The method comprises disposing a plurality of capacitors, which is fewer in number than the plurality of terminal pins, around selected terminal pins in the plurality of terminal pins. Each capacitor in the plurality of capacitors has a predetermined capacitance and is disposed around a different one of the selected terminal pins. The plurality of capacitors is attached to the feedthrough assembly, and each of the selected pins is electrically coupled to its associated capacitor.

BRIEF DESCRIPTION OF THE DRAWINGS

The following drawings are illustrative of particular embodiments of the invention and therefore do not limit the scope of the invention, but are presented to assist in providing a proper understanding. The drawings are not to scale (unless so stated) and are intended for use in conjunction with the explanations in the following detailed descriptions. The present invention will hereinafter be described in conjunction with the appended drawings, wherein like reference numerals denote like elements, and.

DETAILED DESCRIPTION OF THE EXEMPLARY EMBODIMENT

The following description is exemplary in nature and is not intended to limit the scope, applicability, or configuration of the invention in any way. Rather, the following description provides a convenient illustration for implementing an exemplary embodiment of the invention. Various changes to the described embodiment may be made in the function and arrangement of the elements described herein without departing from the scope of the invention.

Figure 1:
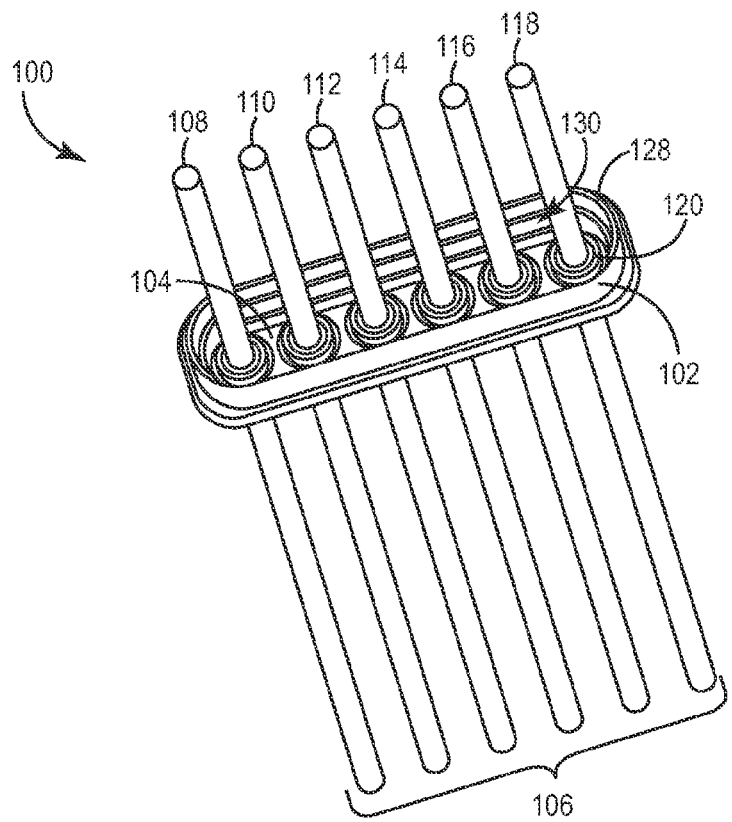
FIGS. 1, 2, and 3 are isometric, top, and cross-sectional views, respectively, of a multipolar feedthrough assembly.
Figure 2:
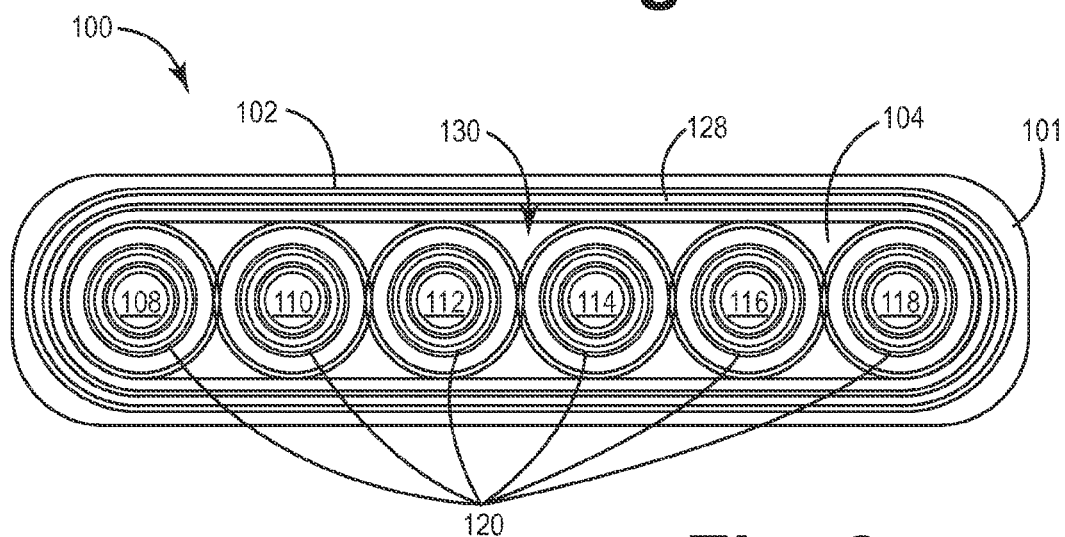
Figure 3:
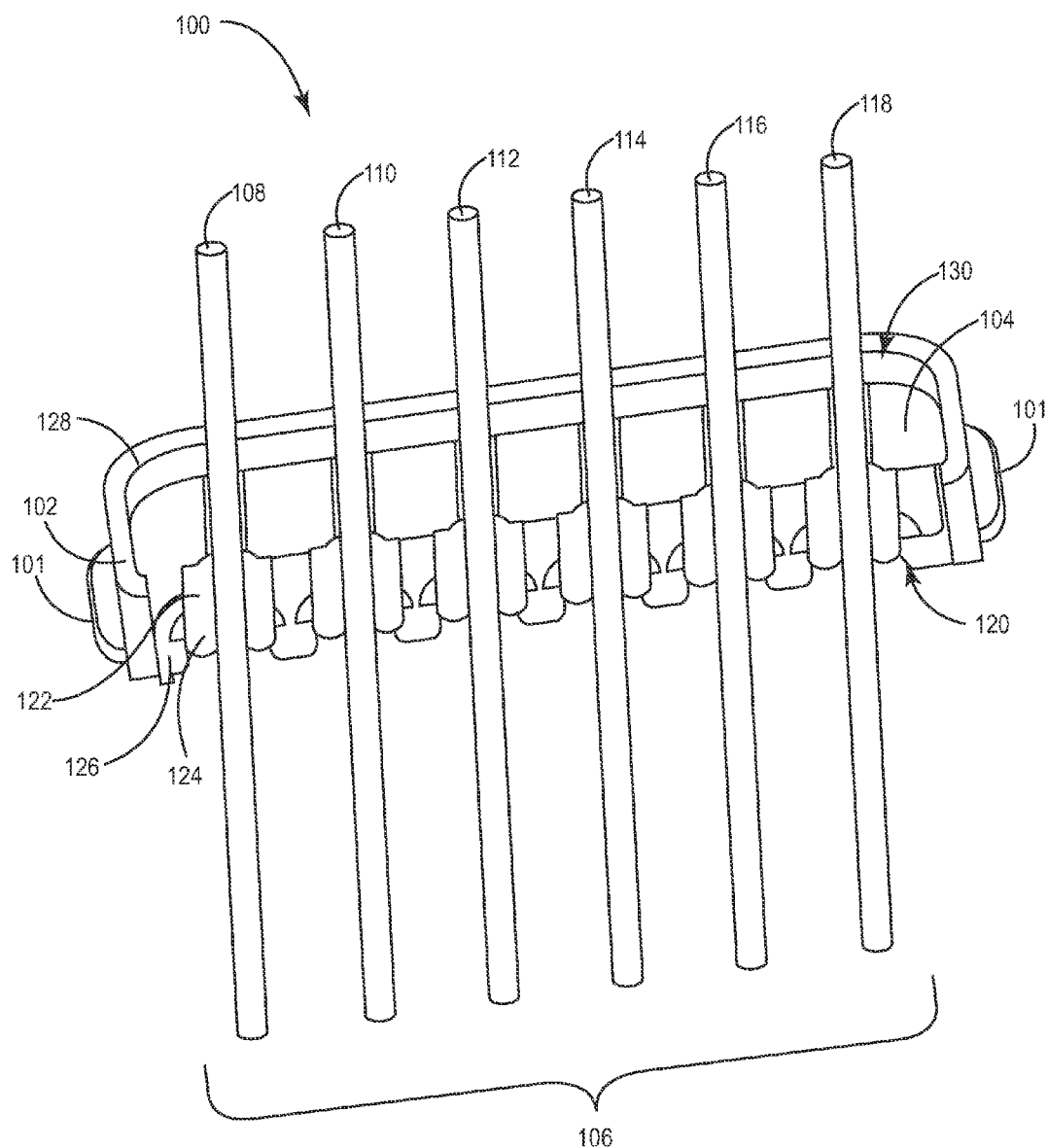

FIGS. 1, 2, and 3 are isometric, top, and cross-sectional views, respectively, of a multipolar feedthrough assembly 100 comprising a ferrule 102 (e.g., titanium, platinum, molybdenum, tantalum, niobium, or other suitable metal/alloy) and a non-conductive supporting structure 104 (e.g., polyimide) fixedly disposed therein. Feedthrough assembly 100 secures and electrically isolates a plurality of electrically conductive terminal pins 106 with respect to a container of a medical device (shown in FIG. 9), such as a cardiac pacemaker, a cochlear implant, a neurostimulator, or the like. Assembly 100 is fixedly coupled to the device's container by welding a flange 101 provided around ferrule 102 to the container of a medical device in the manner described below in conjunction with FIG. 9. In the embodiment illustrated in FIGS. 1–3, terminal pin plurality 106 consists of six terminal pins 108, 110, 112, 114, 116, and 118, which, in this example, are arranged in a row; however, it should be noted that terminal pin plurality 106 may comprise any suitable number of pins arranged in a variety of configurations (e.g., a matrix). As may be most easily appreciated by referring to FIG. 3, the terminal pins of plurality 106 pass through the ferrule 102 and supporting structure 104. A plurality of braze joints 120 is provided beneath structure 104 and within ferrule 102 to secure and electrically isolate the terminal pins of plurality 106. Each braze joint 120 comprises a pin-insulator braze 122 (e.g., gold), an insulator ring 124 (e.g., glass, ceramic, etc.), and an insulator-ferrule braze 126 (e.g., gold), which are each disposed around each terminal pin in plurality 106 in the well-known manner.

Ferrule 102 includes a lip 128 around its upper periphery. Lip 128 and supporting structure 104 cooperate to form a cavity 130 through an upper portion of feedthrough assembly 100. Cavity 130 is configured to partially receive a plurality of capacitors, which serves as an EMI filter for some or all of the terminal pins in plurality 106. The plurality of capacitors may comprise capacitors of various types and capacitances. For example, a plurality of discrete discoidal capacitors may utilized, possibly in conjunction with one or more monolithic discoidal capacitors and/or one or more chip capacitors as described below.

Figure 4:
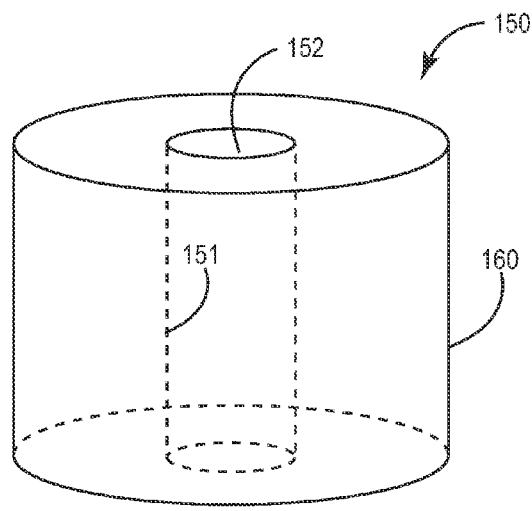
FIGS. 4 and 5 are isometric and cross-sectional views, respectively, of a discrete discoidal capacitor suitable for use in conjunction with the feedthrough assembly illustrated in FIGS. 1–3.
Figure 5:
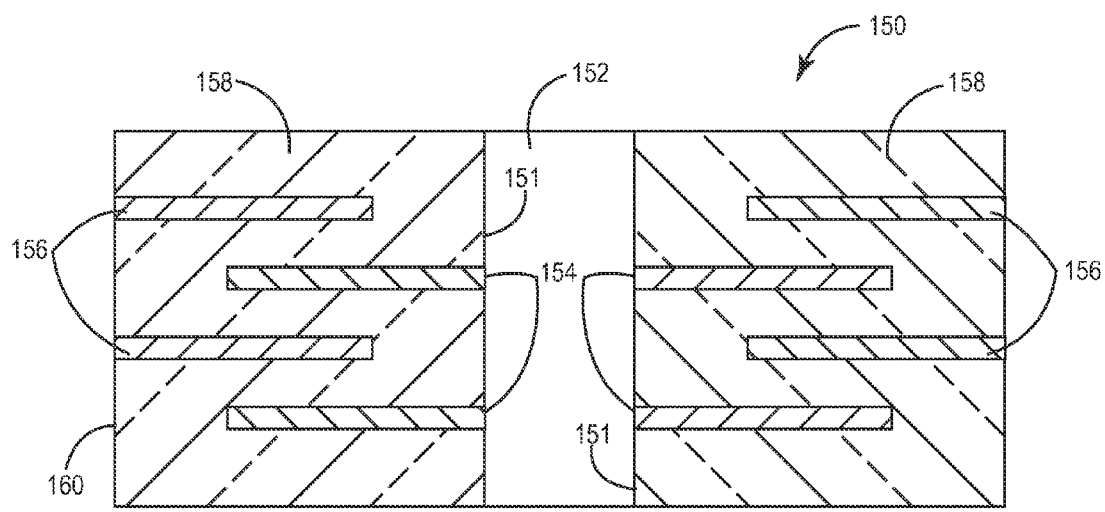

FIGS. 4 and 5 are isometric and cross-sectional views, respectively, of a known discrete discoidal capacitor 150 suitable for use in conjunction with feedthrough assembly 100 (FIGS. 1–3). Capacitor 150 includes an inner annular surface 151 that defines a cylindrical terminal pin aperture 152 that extends from an upper to a lower surface of capacitor 150 as is shown in phantom. Capacitor 150 further comprises a first set of inner electrode plates 154 and a second set of outer electrode plates 156 that are each embedded within an insulative or dielectric base structure 158 in a stacked configuration. The inner peripheral edges of inner electrode plates 154 extend radially inward to inner annular surface 151 and are thus exposed along terminal pin aperture 152. Similarly, the outer peripheral edges of outer electrode plates 156 extend radially outward to an outer surface 160 of capacitor 150. A metallic film (e.g., metalized, silverized, plated, etc.) coats inner annular surface 151 and outer surface 160 and electrically couples inner electrode plates 154 and outer electrode plates 156, respectively.

Figure 6:
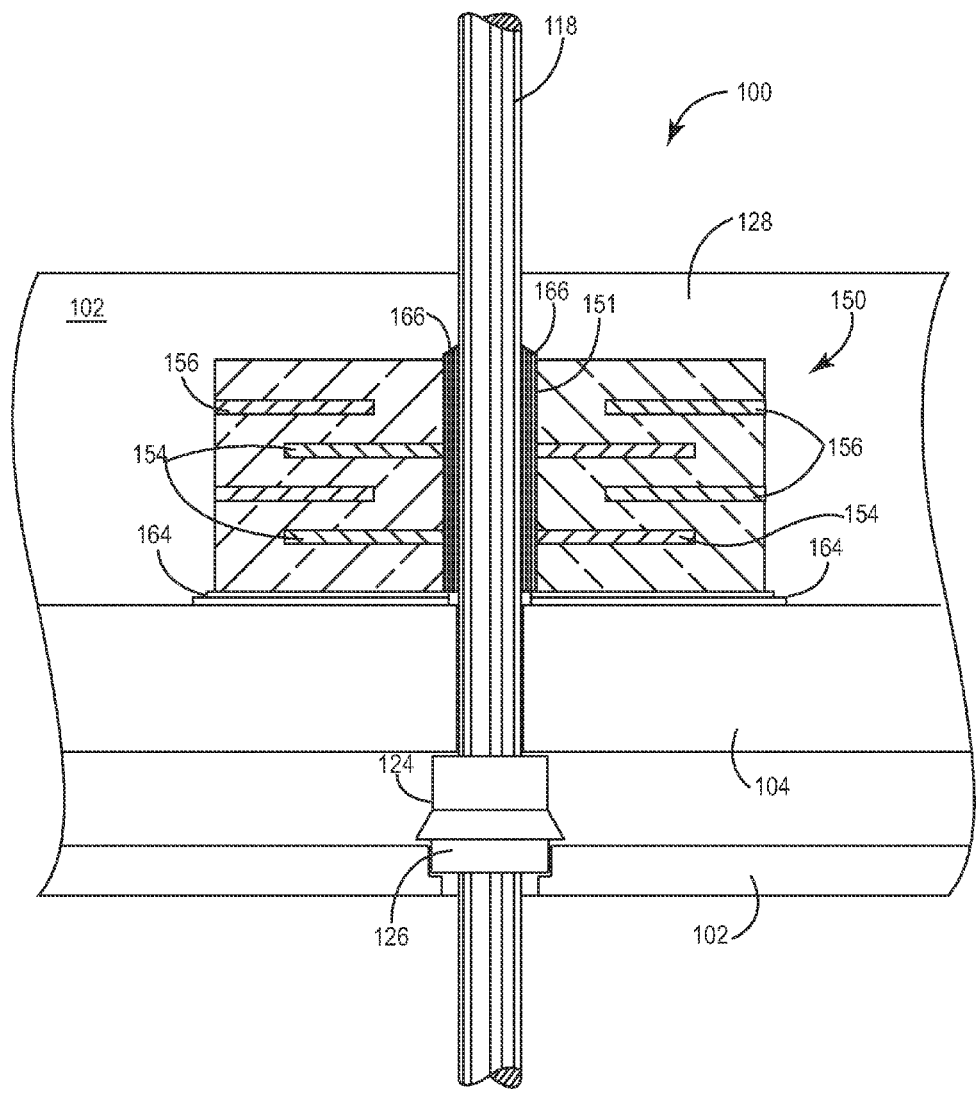
FIG. 6 is a side view, partially in cross-section, of a portion of the feedthrough assembly illustrated in FIGS. 1–3 having the capacitor illustrated in FIGS. 4 and 5 attached thereto.

Capacitor 150 may be threaded over a selected terminal pin (e.g., terminal pin 118) in plurality 106 and placed in an abutting relationship with supporting structure 104 as shown in FIG. 6 (a side view of feedthrough assembly 100 illustrating capacitor 150, supporting structure 104, and ferrule 102 in cross-section). As can be seen in FIG. 6, the inner diameter of terminal pin aperture 152 is larger than the outer diameter of terminal pin 118; thus, when capacitor 150 is threaded over pin 118, an annular cavity is formed between the outer surface of terminal pin 118 and inner surface 151 of capacitor 150. After being suitably positioned relative to ferrule 102 and feedthrough terminal pin 118, capacitor 150 is fixedly coupled to structure 104 and, therefore, ferrule 102. For example, capacitor 150 may be attached to structure 104 by curing an epoxy preform disposed between capacitor 150 and structure 104. More specifically, a ring-shaped epoxy preform having an aperture therethrough may be threaded over terminal pin 118 and positioned within cavity 130 to abut supporting structure 104. Capacitor 150 is then slipped over terminal pin 118 and partially inserted into cavity 130 such that the epoxy preform is sandwiched between the underside of capacitor 150 and the upper surface of structure 104. Next, feedthrough assembly 100 is placed within a curing oven and heated to a predetermined temperature (e.g., approximately 175 degrees Celsius) to melt the preform as shown in FIG. 6 at 164. Lastly, feedthrough assembly 100 is withdrawn from the curing oven and the melted preform is allowed to set thereby securing capacitor 150 in relation to feedthrough assembly 100 and terminal pin 118.

After capacitor 150 has been fixedly coupled to feedthrough assembly 100, outer electrode plates 156 are electrically coupled to ferrule 102 by, for example, soldering capacitor 150 to ferrule 102 or dispensing a fillet of conductive epoxy between capacitor 150 and ferrule 102. Similarly, inner electrode plates 154 are electrically coupled to terminal pin 118 by, for example, dispensing a conductive material (e.g., epoxy, polyimide, solder, etc.) 166 into the annular cavity provided between terminal pin 118 and inner annular surface 151 of capacitor 150. Next, assembly 100 is typically centrifuged to remove any voids present in conductive material 166 and a second curing step is performed. Lastly, a non-conductive top coat (not shown) may be applied to the upper surface of capacitor 150 to decrease the likelihood of high-voltage breakdown. After attachment, discrete discoidal capacitor 150 will function to shunt EMI interference signals to the container of an implantable medical device, such as that described below in conjunction with FIG. 9. In particular, high-frequency EMI signals will travel from terminal pin 118 through conductive substance 166 to inner electrode plates 154. From plates 154, the EMI signals will travel to outer electrode plates 156, to ferrule 102, and finally to the container of the medical device to which ferrule 102 is welded.

Figure 7:
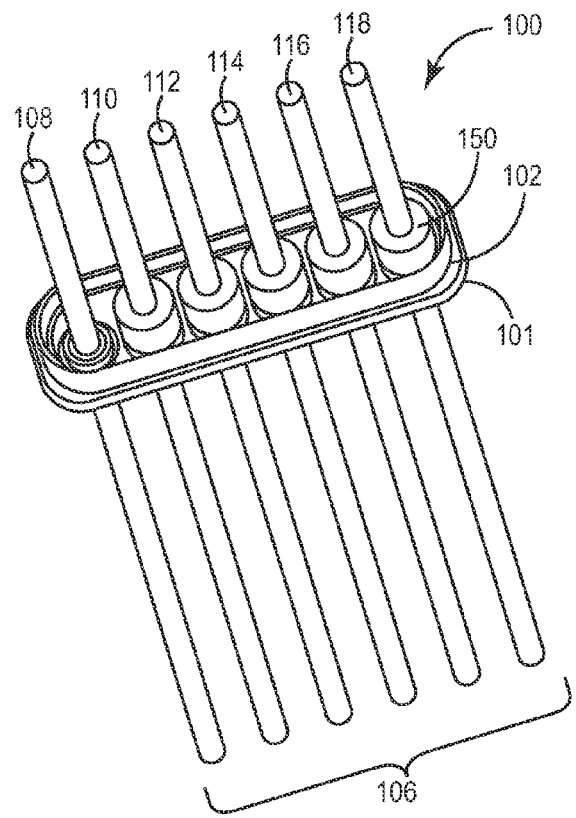
FIGS. 7 and 8 are isometric and top views, respectively, of the feedthrough assembly shown in FIGS. 1–3 having a plurality of discrete discoidal capacitors of the type shown in FIGS. 4 and 5 attached thereto in accordance with a first embodiment of the present invention.
Figure 8:
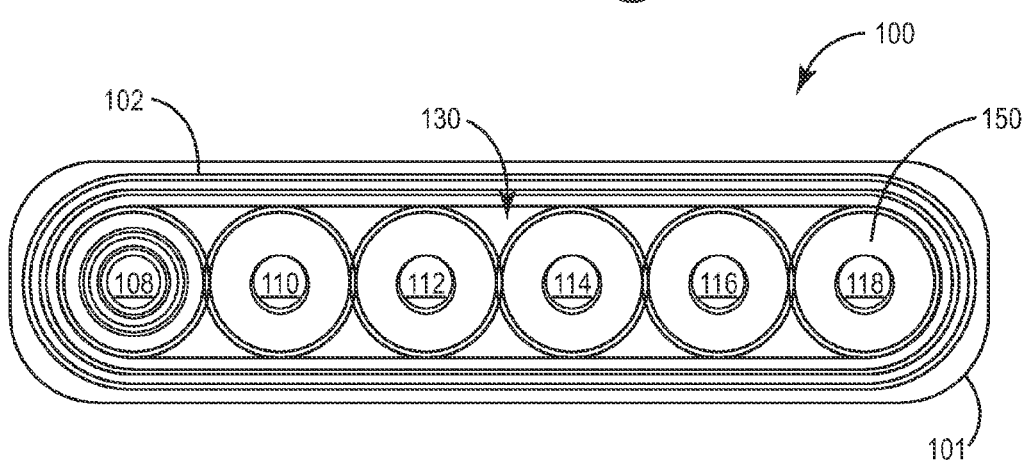

FIGS. 7 and 8 are isometric and top views, respectively, of feedthrough assembly 100 having a plurality of discrete discoidal capacitors 150 disposed around selected terminal pins in plurality 106; for example, capacitors 150 may be disposed around terminal pins 110, 112, 114, 116 and 118 as illustrated. Capacitors 150 may each be chosen to have substantially the same capacitance; alternatively, the capacitance of capacitors 150 may vary from terminal pin to terminal depending upon, for example, the electrical tolerance of the circuitry associated with a particular pin, the susceptibility of each pin to EMI interference, etc. If feedthrough assembly 100 were utilized in conjunction with an implantable pacemaker/defibrillator, for example, multiple pins (e.g., pins 114, 116, and 118) might be utilized for low-voltage (e.g., around 12 volts) sensing/pacing, while other pins (e.g., pins 110 and 112) might be utilized for high-voltage (e.g., around 850 volts) defibrillation. In such a case, each of capacitors 150 disposed around pins 114, 116, and 118 may be low-voltage capacitors (and, therefore, smaller and, perhaps, less costly), while each of capacitors 150 disposed around pins 110 and 112 are high-voltage capacitors. Additionally, terminal pin 108 may serve as an RF antenna to permit communication with an external device and, consequently, may be left unfiltered. Thus, it should be appreciated that by selectively disposing capacitors 150 in this way, feedthrough assembly 100 is customizable in that it may be adapted to a particular application and each terminal pin in plurality 106 may be provided with a pin-specific degree of EMI protection.

Figure 9:
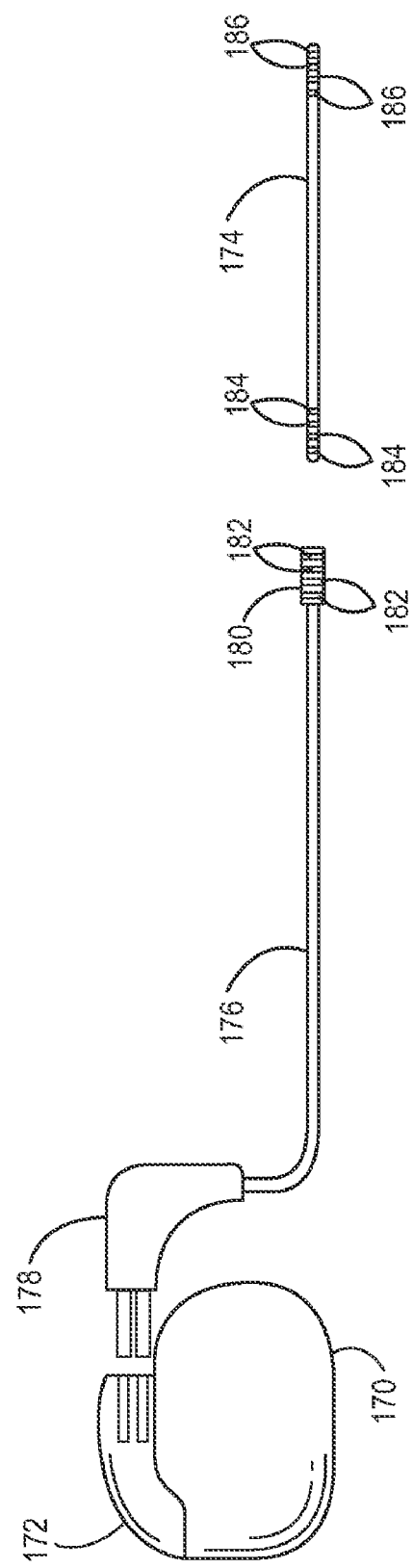
FIG. 9 is an exploded view of an implantable medical device.

FIG. 9 is an exploded view of an implantable medical device including, for example, a pulse generator 170 coupled to a connector block 172 and a lead 174 by way of an extension 176. The proximal portion of extension 176 comprises a connector 178 configured to be received or plugged into connector block 172, and the distal end of extension 176 likewise comprises a connector 180 including internal electrical contacts 182 configured to receive the proximal end of lead 174 having electrical contacts 184 thereon. The distal end of lead 174 includes distal electrodes 186, which may deliver electrical pulses to target areas in a patient's body (or sense signals generated in the patient's body; e.g., cardiac signals).

Figure 10:
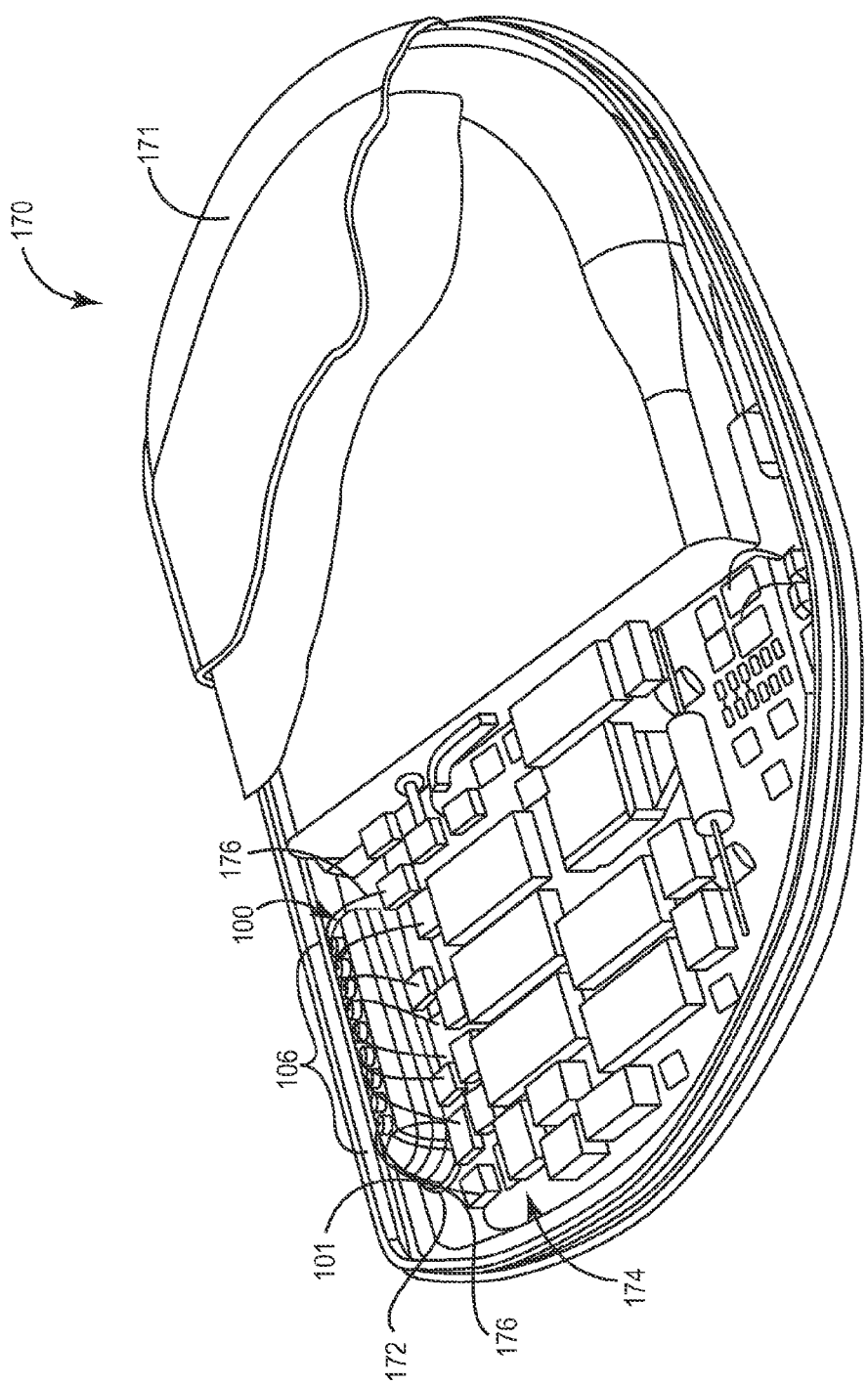
FIG. 10 is an isometric cutaway view of an implantable medical device incorporating the feedthrough assembly shown in FIGS. 1–3, 7, and 8.

FIG. 10 is an isometric view of pulse generator 170 (shown in FIG. 9) comprising a container or housing 171 (e.g. titanium or other biocompatible material) having an aperture 172 therein through which feedthrough assembly 100 is disposed. Feedthrough assembly 100 is fixedly coupled to pulse generator 170 by, for example, welding flange 101 of ferrule 102 to housing 171 proximate aperture 172. As can be seen in FIG. 9, each terminal pin in plurality 106 has been trimmed and is electrically connected to circuitry 174 of pulse generator 170 via a plurality of wires 176 (e.g., gold), which may be coupled to the terminal pins in plurality 106 by wire bonding, laser ribbon bonding, or the like. As described above, feedthrough assembly 100 is equipped with a plurality of capacitors 150 (hidden from view in FIG. 9). Feedthrough assembly 100 and capacitors 150 collectively function to permit the transmission of relatively low frequency electrical signals along the terminal pins in plurality 106 to circuitry 174 while shunting undesired high frequency EMI signals to housing 171 of pulse generator 170.

Figure 11:
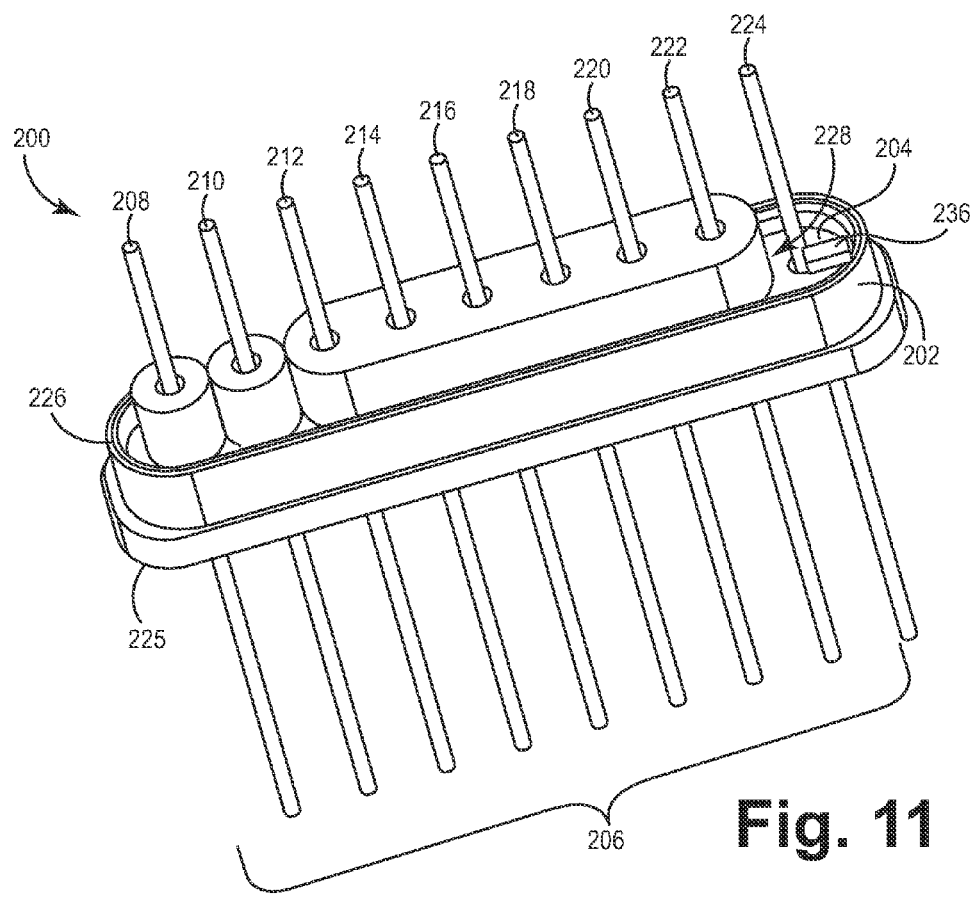
FIGS. 11 and 12 are isometric and top views, respectively, of a multipolar feedthrough assembly having two discrete discoidal capacitors, a monolithic capacitor, and a chip capacitor attached thereto in accordance with a second embodiment of the present invention.
Figure 12:
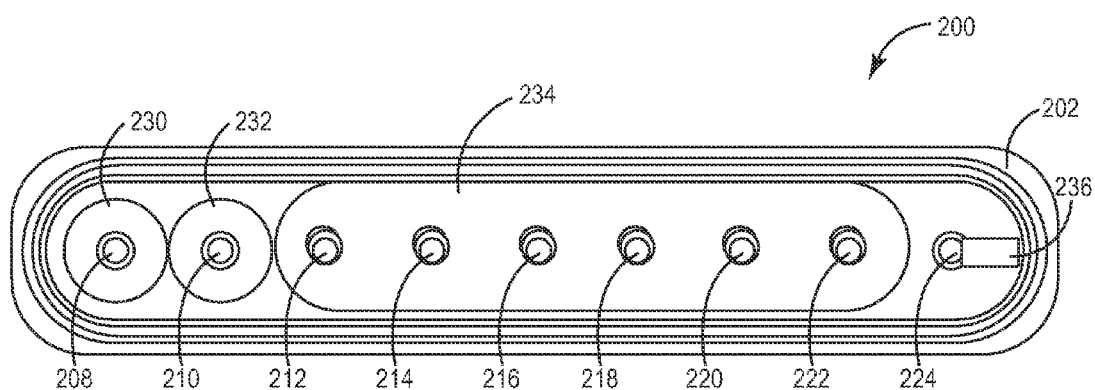

FIGS. 11 and 12 illustrate a feedthrough assembly 200 in accordance with a second embodiment of the present invention. As does assembly 100 described above, feedthrough assembly 200 comprises a ferrule 202, a non-conductive supporting structure 204 disposed within and fixedly coupled to ferrule 202, and a terminal pin array 206 that passes through ferrule 202 and supporting structure 204. In this case, terminal pin array 206 consists of nine terminal pins 208, 210, 212, 214, 216, 218, 220, 222, and 224, which are arranged in a row. Ferrule 202 includes a welding flange 225 and a lip 226 around its upper periphery that cooperates with structure 204 to form a cavity 228 through an upper surface of assembly 200. Multiple capacitors may be positioned within cavity 228 and disposed around or adjacent each terminal pin in array 206 to provide customized degrees of protection from EMI interference (though one or more terminal pins in array 206 may be left unfiltered as described above). In the embodiment illustrated in FIGS. 11 and 12, first and second discrete discoidal capacitors 230 and 232 are disposed around terminal pins 208 and 210, respectively; a monolithic capacitor 234 having a plurality of terminal pin receiving apertures therethrough is disposed around terminal pins 212, 214, 216, 218, 220, and 222; and a chip capacitor 236 is disposed adjacent to terminal pin 224. Capacitors 230, 232, 234, and 236 are each chosen to have a capacitance suited for the terminal pin or pins with which each capacitor is associated. For example, if feedthrough pins 212, 214, 216, 218, 220, and 222 are utilized for a low-voltage sensing and/or pacing application, monolithic capacitor 234 may be chosen to have a relatively low breakdown voltage. Capacitors 230, 232, and 234 are each attached to supporting structure 204 and ferrule 202 utilizing a known attachment technique (e.g., by curing of an epoxy preform as described above). Chip capacitor 236 may be likewise attached or, instead, attached by simply gluing capacitor 236 to structure 204. It should thus be appreciated that, by utilizing a plurality of capacitors of varying types and capacitances, a savings in production cost and volume may be achieved and, furthermore, each terminal pin in plurality 106 may be provided with a customized degree of EMI protection.

It should thus be appreciated from the description above that a multipolar filtered feedthrough assembly having an EMI filter that may be customized for a variety of applications and functions has been provided. Additionally, it should be appreciated that a method for manufacturing such feedthrough assembly has also been provided. Although the invention has been described with reference to a specific embodiment in the foregoing specification, it should be appreciated that various modifications and changes can be made without departing from the scope of the invention as set forth in the appended claims. Accordingly, the specification and figures should be regarded as illustrative rather than restrictive, and all such modifications are intended to be included within the scope of the present invention.

The invention claimed is:

1. A feedthrough assembly for guiding a plurality of terminal pins through a housing of an implantable medical device, the feedthrough assembly comprising:

a ferrule fixedly coupled to the housing and having an aperture therethrough;

a non-conductive supporting structure fixedly coupled to said plurality of terminal pins and disposed within said aperture for guiding said plurality of terminal pins through said ferrule; and a plurality of capacitors fixedly coupled to said supporting structure and electrically coupled between said ferrule and selected ones of said plurality of terminal pins, said plurality of capacitors being fewer in number than said plurality of terminal pins.

2. A feedthrough assembly according to claim 1 wherein said plurality of capacitors includes a first discrete discoidal capacitor disposed around a first terminal pin of said plurality of terminal pins.

3. A feedthrough assembly according to claim 2 wherein said plurality of capacitors further includes a second discrete discoidal capacitor disposed around a second terminal pin of said plurality of terminal pins.

4. A feedthrough assembly according to claim 1 wherein said plurality of capacitors includes at least first and second capacitors having different capacitances.

5. A feedthrough assembly according to claim 4 wherein said plurality of terminal pins includes at least one high-voltage terminal pin and at least one low-voltage terminal pin, and wherein said first capacitor is disposed around said high-voltage terminal pin and said second capacitor is disposed around said low-voltage terminal pin.

6. A feedthrough assembly according to claim 2 wherein said plurality of capacitors further includes a monolithic capacitor disposed around at least second and third terminal pins of said plurality of terminal pins.

7. A feedthrough assembly according to claim 1 wherein said plurality of capacitors includes a chip capacitor disposed adjacent a first terminal pin of said plurality of terminal pins.

8. A feedthrough assembly according to claim 1 wherein said ferrule and said supporting structure cooperate to form a cavity through a surface of said feedthrough assembly, and wherein said plurality of capacitors is partially disposed in said cavity.

9. A feedthrough assembly according to claim 1 wherein at least one terminal pin of said plurality of terminal pins is unfiltered.

10. A feedthrough assembly according to claim 9 wherein said at least one terminal pin is configured to permit radio frequency communication with the implantable medical device.

* * * * *